(12) United States Patent
Blaine

(10) Patent No.: US 8,965,795 B2
(45) Date of Patent: Feb. 24, 2015

(54) METHODS AND SYSTEMS FOR LABELING LABWARE

(76) Inventor: Jill Blaine, Iowa City, IA (US)

( * ) Notice: Subject to any disclaimer, the term of this patent is extended or adjusted under 35 U.S.C. 154(b) by 162 days.

(21) Appl. No.: 13/271,507

(22) Filed: Oct. 12, 2011

(65) Prior Publication Data

US 2012/0089490 A1     Apr. 12, 2012

Related U.S. Application Data

(60) Provisional application No. 61/392,060, filed on Oct. 12, 2010.

(51) Int. Cl.
| | |
|---|---|
| *G06Q 10/00* | (2012.01) |
| *G06Q 10/08* | (2012.01) |
| *B01L 3/00* | (2006.01) |
| *G06Q 50/22* | (2012.01) |

(52) U.S. Cl.
CPC ............ *G06Q 10/087* (2013.01); *B01L 3/54* (2013.01); *G06Q 50/22* (2013.01); *B01L 2300/021* (2013.01)
USPC .......................................... 705/28; 705/7.12

(58) Field of Classification Search
CPC ................... G01N 35/000099; G01N 35/028
USPC ........... 312/400; 700/218; 435/6.12, 29, 6, 12
See application file for complete search history.

(56) References Cited

U.S. PATENT DOCUMENTS

| | | | |
|---|---|---|---|
| 2004/0259111 A1 * | 12/2004 | Marlowe et al. | 435/6 |
| 2007/0174253 A1 * | 7/2007 | Hodnett et al. | 707/3 |
| 2007/0289956 A1 * | 12/2007 | Knysh et al. | 219/121.68 |
| 2010/0323384 A1 * | 12/2010 | Stark et al. | 435/29 |

* cited by examiner

*Primary Examiner* — Scott Zare
*Assistant Examiner* — Rokib Masud
(74) *Attorney, Agent, or Firm* — Simmons Perrine Moyer Bergman PLC

(57) ABSTRACT

The present invention includes a system for marking labware. The system includes an instruction set with markings to be applied to pieces of labware and the order in which the markings are to be applied to the labware. The system also includes a marking device that receives the instruction set and then places the non-toxic marks on the pieces of labware. The invention also includes methods tracking chain of custody of biological material in a facility. The methods include assigning a unique marking for biological materials, storing that marking in a database, applying a non-toxic marking to a piece(s) of labware and then scanning the marking.

6 Claims, No Drawings

METHODS AND SYSTEMS FOR LABELING LABWARE

CLAIM OF PRIORITY

This application claims the benefit of provisional application 61/392,060, filed on Oct. 12, 2010.

FIELD OF THE INVENTION

The invention relates to systems and methods for labeling labware, and more particularly, to systems and methods for labeling labware while maintaining a sterile environment.

BACKGROUND OF THE INVENTION

In vitro fertilization (IVF) is an important technique for providing family planning options. Although a relatively mature area of science, in practice IVF remains expensive and stressful for people. Consequently, IVF personnel are extremely conservative is the adoption of new technologies. In particular, personnel refuse to adopt any technology that could have an adverse effect on the success of an IVF procedure, either through the procedure itself or through the introduction of materials that may be toxic. This reticence extends to every aspect of the procedure including the tools and technologies that play a supporting role in the IVF procedure.

The recent focus on the high cost of health care has placed pressure on all personnel to reduce overhead. Reducing overhead includes streamlining the record keeping. However, the extreme reticence of IVF personnel has lead most personnel to not adopt techniques that would reduce recording keeping costs because of concerns that introducing new technology will introduce new dangers.

One area of concern is the tracking of biological material such as gamete and embryo materials. Since no mistakes are acceptable, there is high importance placed on accurately tracking materials in the fertility clinic and laboratories. These materials typically are handled by several personnel and are moved from location to location multiple times within the facility. Thus, there are several chances for mistakes to be made.

This has led fertility clinics and laboratories to permanently mark containers, such as culture dishes and other labware. Predominately, labware is hand-marked with a carbide tipped stylus. The markings on the culture dishes are often repeated on the top (lid) of the dish and on the bottom of the dish and the markings consist of anywhere from 10-100 characters (approximately). Hand engraving the culture dishes consumes thousands of hours of staff time. Hand engraving is open to errors in duplication because the engraving has to be completed up to twenty times for each procedure. Moreover, this process is usually completed in a sterile environment and thus is not amenable to completion by less trained staff and is usually completed by an embryologist or laboratory technician, so as to preserve the sterile, non-toxic environment of the dishes and the laboratory.

The present invention overcomes one or more of these problems.

SUMMARY OF THE INVENTION

The present invention includes a system for marking labware. The system includes an instruction set with markings to be applied to pieces of labware and the order in which the markings are to be applied to the labware. The system also includes a marking device that receives the instruction set and then places the non-toxic marks on the pieces of labware. The invention also includes methods tracking chain of custody of biological material in a facility. The methods include assigning a unique marking for biological materials, storing that marking in a database, applying a non-toxic marking to a piece(s) of labware and then scanning the marking.

DETAILED DESCRIPTION

The present invention includes a system for the addition of a non-toxic marking on labware.

Labware includes all containers that may be utilized in a clinical or laboratory environment. Labware is a general term that encompasses container that are made of glass, plastic, metal, etc. Exemplary labware includes culture dishes that included a top or lid and a bottom, as well as sample vials and test tubes and their associated caps or covers. Labware also includes wrist bands utilized to identify clients during client visits to the facility. While labware generally includes only single use or disposable containers, multiuse containers are also contemplated.

Non-toxic generally means that the success of the IVF or other medical, surgical, diagnostic or research procedures performed in the facility will not be adversely effected by the introduction or presence of the marking. Non-toxicity can be shown through FDA approval, manufacturer certification or other means.

The system includes at least an instruction set and a marking device.

The instruction set is information that is useable by the marking device to apply one or more markings to labware. The instruction set includes information about the nature of the marking to be applied, the type of material that makes up the particular piece of labware, the positioning of the marking on a particular piece of labware, and positioning of a particular piece of labware within a work area of the marking device.

The marking includes both human readable and non-human readable markings. Human readable markings may include information, such as client name, social security number, birth date, medical record number (MRN), donor record number, third party reproduction information, specimen number, specimen ID, etc. Non-human readable markings include barcodes. Barcodes include all one, two and three dimensional markings that may be visible to the naked eye and/or read with a scanner and preferably with an optical scanner. Barcode also includes a string of information that may be read with a radio frequency scanner. For example, RFID tags may include barcodes in the information that they store and/or transmit. Barcodes are utilized because they are easily associated with specific client information and need to be assigned only once. Barcodes also tend to contain a plethora of information in a relatively small space, and yet are reliably reproducible.

In a preferred embodiment, a two-dimensional or matrix barcode is utilized that is visible to the naked eye and readable by an optical scanner. The 2D barcode includes a pattern of opaque cells or modules arranged on the labware. The data to be encoded can be text (no matter what script or language) or numbers and the data size ranges from a few bytes up to several thousand bytes. The amount of the encoded data depends on the type of symbol used in the barcode (e.g. square, triangles, hexagon, circles, etc), the number of symbols used and whether different colors of symbols are utilized. The 2D barcode may stores 2,335 or more alphanumeric characters. However, a barcode storing between 12 and 24 alphanumeric characters is preferred because it is relatively small in area and yet contains enough information to identify the biological material in the labware.

In one embodiment for use in fertility facilities, the data encoded in the 2D barcode is a marriage of identifying information about the female gametes and the male gametes. The identifying information may include the MRN, source record number, other information that uniquely identifies the source of the gametes, or other information that uniquely identifies the source record of the gametes. In one example, the female MRN and the male MRN are concatenated together to produce the information that would then be used to make the 2D barcode. On occasion, the information used to make the barcode is too voluminous to produce a barcode that will be appropriately sized for the piece of labware. Thus, a subset of information may be used, provided that the subset of information still results in a unique barcode. Moreover, information may used in the barcode concerning one set of gametes that is the combination MRNs of multiple people; for example, when a same-sex male couple both donate gametes to be used with a donated female gamete. Moreover, the process of generating the barcode may be reversible so that the individual MRNs (or other identifying information) are retrievable. In this manner, a found piece of labware can be properly associated with any individual(s). Thus, the chain of custody of a piece of labware is always available or reproducible, thus reducing or eliminating errors in the facility.

Error correction information may be added to the information from which the barcode is created, so that even if a portion (e.g. up to 40%) of the barcode is damaged, the information can still be retrieved from the barcode.

The marking, particularly the human readable portion, may be modified depending on the type of labware that is being marked. For example, only a partial client name may be used on space constrained labware. The non-human readable information may also be modified in such an instance. For example, the amount of information encoded in the barcode may be reduced (e.g. reduced error correction information or reduced information identifying the biological material), thus permitting a barcode with a smaller area.

In one preferred embodiment, the marking includes a mirror image of another marking to be placed on a piece of labware. In this embodiment, the mirror image marking will appear in the proper orientation when viewed or scanned through the side or the top of the piece of labware, e.g. a culture dish. This is desirable for the facility personnel because the marking can be read without having to raise the labware overhead to read the bottom of the labware or without having to flip the labware over. Both actions could cause damage to the contents of the labware.

The instruction set may include human readable markings, non-human readable markings or combination of these markings. The instruction set may include the markings per se (e.g. images), may include information needed by the marking device to reproduce the markings on the labware, or combinations thereof.

The instruction set may also include information on the type of material that makes up the particular piece of labware, e.g. glass, metal or plastic. In this manner, settings appropriate for the particular material may be utilized by the marking device. For example, the laser settings for marking glass may be different from the laser setting for marking plastic (or even two different types of plastic). Matching the marking device settings to the particular material will help insure that the markings will be consistently readable.

The instruction set may also include information on the positioning of the marking on a particular piece of labware. For example, the placement of a marking on a culture dish will be different than placement on a sample vial. Proper positioning information will help insure that the markings will be consistently readable. While it is preferred that markings are placed on roughly flat surfaces of labware, this is not always possible because the available flat surface is too small or there is no flat surface of the labware. For example, on a culture dish, the marking may be placed on the rim of the top or bottom plate. This would insure that the marking would not hinder inspection of the contents of the dish (e.g. under a microscope). In an alternative, the marking can be placed circumferentially along the edge of the top or bottom plate so as to provide a greater field of view.

The instruction set may also include information on the position of individual pieces of labware within the work area of the marking device. This permits batch marking of labware. A plurality of different markings (represent different clients of the facility) may be applied to a batch of identical pieces of labware (e.g. all culture dishes). A plurality of the same markings (representing the same client) may be applied a batch of various pieces of labware (e.g. culture dishes, sample vials, wrist bands, etc.). Of course, different markings may be applied to a batch of various pieces of labware.

The information in the instruction set may be organized so as to increase the efficiency of the marking. For example, the information could be organized by client information so that all the labware for a particular client's procedure is marked in a batch. In the alternative, the information could be organized by labware type so that labware of the same type is marked in a batch. In addition, other ways to organize the information in the instruction set are also contemplated, such as by client's scheduled appoint, by facility personnel, by procedure, etc. Being able to organize the instruction set for primacy of client information and for primacy of labware type provides flexibility while also achieving economies of scale. Of course, the instructions set could be sorted to combine client information, labware type, client schedule, etc.

While not required, the present marking system may be used with sterile labware, where sterile generally means that the environment is free of pathogens. This is particularly, desirable in the fertility area, given the delicacy and expense of the procedure.

In one family of embodiments, the marking is a part of the labware such as molded into the labware or engraved into the labware. In both embodiments, labware would not needed to be opened during the marking process, thus preserving the sterility of the environment within the labware.

The marking device may include a rotary or laser engravers. These marking devices include a stylus, which is the portion of the device that physically modifies the labware. For a rotary engraver, the stylus would be like a drill bit or other rotating grinding tool. For a laser engrave, the stylus would be where the laser exits the device. These are particularly well suited for use on labware because of the precision with which these devices can render markings. For example, the stylus of these engravers can render marking having up to 1200 dpi or more. An engraver is suitable because, when connected to an appropriately programmed computer, it can reliably reproduce a marking (e.g. a barcode) across several pieces of labware as well as reliably produce innumerable different markings on different pieces of labware. Engraving is a known and accepted non-toxic method of marking labware and does not introduce any new materials into the procedure. The engraver is easily scalable also permitting increased marking of labware as client volumes increase. Furthermore, an engraver permits labware to be marked at the time of use or onsite at the facility. This permits customization of the marking process to meet the needs of individual facilities.

Each marking device operates within reach of the stylus. This so called work area may be integrated into or separate from the rest of the marking device. The work area may simple be a predefined area on the work bench in which labware is placed to be marked. In the alternative, the work area may be a tray or other open, roughly-flat, container to sequester the labware from the remainder of the work bench. The work area may include a mat, template or other material which help prevent the labware from moving during the marking operation. While not critical for a laser engraver, it is preferred for a rotary engraver. For example, a small-form, desktop model of an engraver, the work area that could hold four to eight 60×15 mm culture dishes at a time. A larger work area could hold up to sixteen 60×15 mm dishes.

In one embodiment, a laser engraver is utilized. A laser engraver has several advantages including being able to engrave multiple types of materials such as glass and plastic. While any laser engraver capable of writing the barcode may be utilized, it is preferred that the laser engraver be capable of marking the labware without damaging the material of the labware. For example, with a laser that is too powerful, plastic labware will not be marked, but rather the laser will just melt the plastic, rendering the marking unreadable. Reducing the fidelity of the barcode increases read error rates, and thus increases the cycle time of reading the barcodes.

Moreover, it is preferred that the laser engraver include an optics system that permits a suitable balance between DPI and power of laser while limiting damage to the material of the labware. For example, one preferred engraver is a CO2 laser engraver that utilizes the radiance high definition optics system found in some Epilog laser engravers. These lasers have a more perfectly circular shape to their beam, maintain that circular shape over the entire engraving operation, have a small spot size, and have a higher power density. One preferred laser engraver is the Epilog Mini24 laser engraver system.

In another embodiment, the labware is manufactured with a barcode in the material of the labware. For example, barcodes (e.g. bumpy barcodes) could be molded into glass or plastic culture dishes at the time of manufacture. Such markings have the same ability to be used to track chain of custody as engraved markings. The bumpy barcodes may or may not be unique on each piece of labware. For example, there may be an advantage to having several pieces of labware marked with the same barcode. Bumpy barcodes would be non-toxic and thus non-controversial because they do not introduce any new materials into the procedure.

In a second family of embodiments, the barcode is attached to the labware. Attachment includes adhesive attachment, embedding as well as using a physical fastener.

In one embodiment, an RFID tag (including an integrated circuit and an antenna) may be adhesively attached to the labware. The RFID tag stores the barcode and responds with the barcode when interrogated. In the alternative, an RFID tag may be embedded in the labware at the time of manufacturing. Placement of the RFID tag is preferably similar to placement of the engraved barcode.

Any of active, passive or programmable RFID tags may be used, depending on the non-toxicity of the RFID interrogator. One advantage of the embedded RFID tag over the bumpy barcode is that each piece of labware can be given a changeable barcode.

In another embodiment, a barcode is printed on paper and a non-toxic adhesive is applied to the paper or the labware, with the label then attached to the labware. The paper maybe sterile or otherwise sterilized prior to or after printing of the bar code. The labels maybe pre-printed or printed on demand.

Likewise, the label may have adhesive pre-applied or applied on demand. Such labels are easy to use because they can be applied without exposing the contents of the culture dish. Moreover, the adhesive can be placed on the printed side so that the bar code can be visualized through the bottom of the culture dish. These labels may be placed in a similar manner to the engraved barcodes. Exemplary labels with non-toxic adhesives are those provided under the name Zebra 8000T or HC10000688.

In another embodiment, a barcode on sterile paper is attached to the labware with a physical fastener such as wire or zip tie. A loop located on the piece of labware, e.g. one or both of the top and bottom of the culture dish, maybe used to attached the paper label to the labware. The wire or zip tie are preferably made of known non-toxic materials and are easily sterilizable or otherwise easy to maintain in a sterile condition.

In addition to an instruction set and a marking device, systems of the present invention may also include additional components such that the system is useful in providing a chain of custody for biological material used in procedures at the facility. Chain of custody of biological material is of critical importance in the medical field in general and especially in the fertility field because errors have lifelong and life altering consequences.

One or more scanners may be used to enhance the chain of custody tracking ability of the system. Suitable scanners include those that are capable of reading the non-human readable markings created by the marking device. Suitable scanners include those that capture or respond to reflected energy. Exemplary devices may include imaging sensors such as photodiodes, charge-coupled devices, contact image sensors, photomultiplier tubes, etc. In one embodiment, the scanner also provides a source of energy, such as a laser or other visible light so that the scanner is the source of the energy that is then reflected back and captured by the scanner. In another embodiment, the scanner responds to reflected ambient energy.

For visible barcodes, optical scanners will accomplish this task. For RFID tags, a RF scanner will accomplish this task. While the scanner may also read the human readable marking on the labware, this is not required. Indeed, the complexity and cost of the scanner can be reduced by excluding this functionality. Optical scanners (and thus visible barcodes) are preferred because the light recognized by these scanners is generally accepted as non-toxic. While unclear whether there is an issue, questions surround the safety of using ultraviolet or radio frequency scanners in connection with biological material. By using a scanner that is generally considered safe, acceptance of the scanner by the profession will be increased. Exemplary scanners include those from Cognex and the 8000 series in particular for culture dishes, vials, etc. and a 750 series for paperwork, etc.

In addition to the scanner, the system may also include software with one or more of the following components: a database component, a marking component and scanning component (communicates with the database to track the barcode). The database component will store the needed information for producing the instruction set. In addition, the database also contains information regarding the client's scheduled procedure at the facility. Associated with each procedure is a labware count detailing the type and number of culture dishes, vials, etc. needed for that procedure or client.

Based on the client identifying information and procedure information, the instruction set for the engraver can be produced by the marking component. While usually separate from the database component, the functionality of the marking component may never the less be carried out by the data base component. Likewise, while typically part of the marking component, the functionality of creating the barcode may be part of the database component or a separate component altogether. The instruction set generated by the marking component is structured so that a print driver for the marking device can pass the instructions in the instruction set to the marking device.

The software for the system may be any stock or custom programs or set of programs running on an appropriately programmed general purpose computer. For example, an Access database running on the windows operating system would be a suitable database component.

The scanning component of the software communicates the information read by the scanner to the database component, where the information may be stored, further manipulated or otherwise acted upon.

In one preferred embodiment, some or all of the labware for one client's procedure is loaded into the marking device in one batch and marked. Here, the instruction set would also include the arrangement of the myriad of labware pieces in the marking device's work area. In another embodiment, the information from several clients is gathered together into the instruction set. In this manner, only one type of labware (e.g. culture dishes) are loaded into the area and marked in one batch.

Methods according to the presenting invention include assigning a marking to a client of a facility, storing that marking in a database connected to a marking device, applying the marking to a piece of labware with the marking device, and scanning the marking on the piece of labware.

EXAMPLES

Example 1

A sample database of 23 test clients was used for testing the marking device and scanner. Although some testing was completed using shorter last names, to emulate the "real-world" data as accurately as possible, about half the dish markings included longer and hyphenated, last names.

An Epilog 24 mini 30 watt laser engraver, with radiance high definition optics, was utilized for the marking. Basic settings included using auto focus, a resolution of 200 dpi on a raster setting with the power set at 20% and the speed set at 10%.

A Cognex DataMan 8500 series optical scanner was utilized for the scanning. Basic settings including using all light pipes with light pipe and bright field intensity set to the maximum.

Laser Marking Details and Scanner Results

| Dish size | Dish part | # marked | Time elapse | Scan Results |
| --- | --- | --- | --- | --- |
| 60 × 15 mm | top | 30 | 4:32 (9.1/dish) | No errors |
| 60 × 15 mm | bottom | 30 | 4:32 (9.1/dish) | No errors |
| 60 × 15 mm | top | 35 | 5:44 (9.8/dish) | No errors |
| 60 × 15 mm | bottom | 35 | 5:44 (9.8/dish) | No errors |

Example 2

| Dish size | Dish part | # marked | Time elapse | Scan Results |
| --- | --- | --- | --- | --- |
| 100 × 20 mm | top | 15 | 3:35 (14.3/dish) | No errors |
| 100 × 20 mm | bottom | 15 | 3:33 (14.3/dish) | No errors |
| 100 × 10 mm | top | 15 | 3:34 (14.3/dish) | No errors |
| 100 × 10 mm | bottom | 15 | 3:33 (14.3/dish) | No errors |

As can be seen, marks made using 200 DPI and 20% power were fully readable by the scanner.

The next example was conducted to provide a baseline for the speed and reliability of scanning.

Example 3

60×15 mm dishes (tops and bottoms) non-welled
Conditions: normal—constant ambient air temperature of 76 F (58 C)
Scanning duration: 12 minutes
Number scanned: top of 100 dishes
Scanner Results: 100% read rate with no errors (non-reads)

The next four examples were conducted to evaluate the effects of condensation, as it relates to the readability of the markings. The condensation condition for the examples were created by exposing the dishes to extreme temperatures, but the intent was to emulate any condensation that may occur in the facility, as the dishes are moved from the incubators to the ambient air temperature. It was found that a freeze-thaw type scenario created more "extreme" conditions; thus providing a better level of condensation, to test the scanning of the marked labware.

Culture dishes with condensation, created with freeze/thaw conditions. These dishes were stored at 0 F (−18C) for 30 minutes, then exposure to ambient air, prior to scanning the marks.

Example 4

100×20 mm dish (top and bottom) non-welled
Conditions: 0 F (−18C) for 30 minutes, then exposure to ambient air
Scanning duration: 5 minutes
Number scanned: top of 30 dishes
Scanner Results: 100% read rate with no errors (non-reads).

Example 5

60×15 mm dish (top and bottom) non-welled
Conditions: 0 F (−18C) for 30 minutes, then exposure to ambient air
Scanning duration: 4 minutes
Number scanned: top of 30 dishes
Scanner Results: 100% read rate with no errors (non-reads).

Example 6

60×15 mm dish (top and bottom) welled
Conditions: 0 F (−18C) for 30 minutes, then exposure to ambient air
Scanning duration: 4 minutes
Number scanned: top of 30 dishes
Scanner Results: 100% read rate with no errors (non-reads)

The next example was conducted to evaluate the effects of heavy mineral oil drops, as it relates to the readability of the laser marked barcodes. Mineral oil is often used in combination with biological material in labware. All marks were placed on the perimeter of the dishes and do not interfere with the viewing area of the dishes.

Example 7

100×15 mm dish (tops and bottoms) non-welled with oil drops
Conditions: normal—constant ambient air temperature of 76 F (58 C)
Scanning duration: 6 minutes
Number scanned: tops of 30 dishes
Scanner Results: 100% read rate with no errors (non-reads)

As can be seen, the invention provides a system that can reliably mark labware and reliably read the marked labware. Reliable marking and scanning is critical to providing error free chain of custody needed in a facility.

As used in this specification, 'read', 'scan', 'inspect' and their related forms all refer to visual inspection by facility personnel, with or without the aid of an external magnifier and also to the use of a device which scans the labware for a markings such as an optical scanner or a RF scanner.

Furthermore, the present system may be expanded to include tracking of paper records, equipment and supplies and so it is contemplated that the scope of labware also includes these types of items. While different types of marking devices may be utilized, such as document printers or label printers, the same marking may be used across all types of labware to insure the chain of custody is maintained.

While the specification discusses the present invention in the context of fertility facilities, it is contemplated that the systems and methods may be used in any facility, clinic or laboratory setting in which chain of custody of biological materials is important and it is contemplated that the definition of facility incorporates all of these situations.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method of tracking movement of labware containing biological materials in a facility, comprising:
    assigning a unique marking to each of a plurality of gametes or embryos, wherein each marking identifies a source record for each gamete or embryo, wherein the source record comprises information about at least one female gamete or at least one male gamete;
    storing the markings, or information representing the markings, in a database connected to a laser engraver;
    engraving with the laser engraver at least one of the markings onto one or more pieces of labware;
    scanning, with an optical scanner, at least one marking on at least one piece of labware before or after transferring the at least one piece of labware from one location to another,
    wherein the marking is a barcode.

2. The method of claim 1 wherein the marking further comprises one or more human readable markings.

3. The method of claim 2 wherein the source record of one or more gametes or embryos comprises: a) one or more medical record numbers, b) one or more source record numbers, c) information that uniquely identifies the source of the gametes or the embryo, or 4) combinations thereof.

4. The method of claim 1 further comprising placing at least one gamete or embryo into at least one piece of labware, either before or after the engraving step.

5. The method of claim 4 further comprising repeating the scanning step at multiple locations.

6. The method of claim 1 wherein the sterility of an interior space of the one or more pieces of labware is maintained during the engraving step.

\* \* \* \* \*